(12) United States Patent
Listgarten et al.

(10) Patent No.: US 8,473,218 B2
(45) Date of Patent: Jun. 25, 2013

(54) REFINING HLA DATA

(75) Inventors: Jennifer Listgarten, Santa Monica, CA (US); David Earl Heckerman, Santa Monica, CA (US); Carl M. Kadie, Bellevue, WA (US)

(73) Assignee: Microsoft Corporation, Redmond, WA (US)

( * ) Notice: Subject to any disclaimer, the term of this patent is extended or adjusted under 35 U.S.C. 154(b) by 594 days.

(21) Appl. No.: 12/431,786

(22) Filed: Apr. 29, 2009

(65) Prior Publication Data

US 2010/0191513 A1    Jul. 29, 2010

Related U.S. Application Data

(60) Provisional application No. 61/148,317, filed on Jan. 29, 2009.

(51) Int. Cl.
*G01N 33/50* (2006.01)

(52) U.S. Cl.
USPC .......................................................... 702/19

(58) Field of Classification Search
None
See application file for complete search history.

(56) References Cited

U.S. PATENT DOCUMENTS 7,653,491 B2 * 1/2010 Schadt et al. ................... 702/20
2004/0203023 A1 * 10/2004 Chandrasiri Herath .......... 435/6

OTHER PUBLICATIONS

Listgarten et al., "Statistical Resolution of Ambiguous HLA Typing Data", 2008, PLOS Computational Biology, vol. 4, Issue 2, pp. 1-15.*
Tongio et al., "Genotypage HLA: indications et limites", 1998, Transfus Clinique et Biologique, vol. 5, No. 1, pp. 6-12 (abstract in English).*

* cited by examiner

*Primary Examiner* — Jason Sims

(57) ABSTRACT

A system described herein includes a receiver component that receives an HLA data set, wherein the HLA data set comprises low resolution HLA data. An HLA refinement component comprises a statistical model that automatically refines the HLA data set to transform the low resolution HLA data to high resolution HLA data.

20 Claims, 10 Drawing Sheets

FIG. 3

| patientId | A | A | B | B | C | C |
|---|---|---|---|---|---|---|
| T1 | A*0201 | A*0201 | B*4402 | B*4402 | C*0501 | C*0501 |
| T2 | A*0201 | A*0201 | B*4403 | B*1501 | C*0102 | C*1601 |
| T3 | A*0201 | A*0201 | B*1501 | B*1501 | C*0303 | C*0304 |
| T4 | A*0101 | A*2402 | B*0801 | B*0801 | C*0602 | C*0701 |
| T5 | A*0101 | A*3101 | B*0801 | B*5701 | C*0501 | C*0701 |
| T6 | A*0201 | A*2402 | B*4001 | B*4001 | C*0304 | C*0304 |
| T7 | A*2402 | A*1101 | B*0702 | B*3501 | C*0401 | C*0702 |
| T8 | A*0101 | A*6801 | B*4403 | B*2705 | C*0102 | C*0401 |
| T9 | A*0201 | A*0201 | B*4402 | B*4001 | C*0304 | C*0501 |
| ... | ... | ... | ... | ... | ... | ... |
| T1000 | A*0101 | A*3101 | B*5701 | B*4001 | C*0304 | C*0602 |

FIG. 4

| patient | A1 | B1 | C1 | A2 | B2 | C2 |
|---|---|---|---|---|---|---|
| P200 | A*0201 | B*2705 | C*0703 | A*6801 | B*0701 | C*0701 |

REFINING HLA DATA

RELATED APPLICATION

This application claims the benefit of U.S. Provisional Patent Application No. 61/148,317, filed on Jan. 29, 2009, and entitled "REFINING HLA DATA." The entirety of this application is incorporated herein by reference.

BACKGROUND

Human Leukocyte Antigen (HLA) typing (determining specific HLA alleles which an individual expresses at each class I and/or class II loci) is a useful tool for basic and clinical immunology research. For instance, HLA typing has been used to identify immunogenetic risk factors for human diseases and more recently has been used to investigate how pathogens (such as HIV) evolve in response to HLA-restricted immune selective pressures. HLA typing may also be useful in connection with vaccine research—the identification and mapping of HLA-restricted T-cell epitopes in the proteomes of difference pathogens may be used to inform a selection of potential immunogens in a T-cell based vaccine design. Further, HLA typing may be used in connection with transplantation medicine, such as for hematopoietic stem cell transplants: in order to minimize risk of rejection, donors and unrelated recipients are desirably matched with respect to HLA alleles.

HLA typing has conventionally been performed using low-resolution antibody-based serological tests. In addition, HLA typing can be achieved using molecular (DNA-based) methods. Molecular methods for HLA typing include hybridization with sequence-specific oligonucleotide probes, PCR amplification with sequence-specific primers, and DNA sequence-based methods.

Due to a relative high (and ever-increasing) number of identified HLA alleles (and thus growing list of ambiguous combinations), unambiguous HLA typing is costly, laborious, and limited to laboratories specializing in this work. For the purposes of scientific research, HLA types are often not unambiguously determined—rather, they are determined up to some "resolution" (level of ambiguity). Additionally, because the number of HLA alleles is constantly increasing, sequence-based, SSOP and SSP based typing results, which depend on the list of known alleles, require constant re-interpretation in light of newly-discovered alleles. This re-interpretation can result in more ambiguity than originally thought, and it is often impossible to re-type historic samples that may have been typed using lower-resolution approaches.

The practical consequence of these issues is that there is a large incongruence between the high-resolution HLA typing required for scientific investigations and the HLA typing that is widely available.

SUMMARY

The following is a brief summary of subject matter that is described in greater detail herein. This summary is not intended to be limiting as to the scope of the claims.

Described herein are various technologies pertaining to human leukocyte antigen (HLA) refinement, wherein HLA refinement refers to automatically transforming low resolution HLA data to high resolution HLA data. Low resolution HLA data is HLA data resolved to two numerical digits to represent allele types and high resolution HLA data is HLA data resolved to at least four numerical digits to represent allele subtypes.

As described in detail herein, a statistical model can be employed in connection with automatically transforming low resolution HLA data to high resolution HLA data. Pursuant to an example, such a model can be trained through use of unphased high resolution HLA data, wherein the unphased high resolution HLA data used to train the model may correspond to a particular ethnic group or geographic location. In another example, high resolution HLA data used to train the model may correspond to a general population or multiple (selected) ethnic backgrounds. Furthermore, when training the model, phase of the unphased HLA data can be inferred.

With respect to the statistical model, an expectation-maximization algorithm can be used in connection with training the statistical model and inferring phases of the unphased data. In another example, a Monte Carlo algorithm can be used in connection with training the statistical model as well as inferring phases of the unphased data. Furthermore, the statistical model may use one or more multi-logit regression functions.

Once the model has been trained, such model can be configured to receive a data set that includes low resolution data (e.g., phased or unphased). Pursuant to an example, low resolution HLA data can be expanded such that all possible refinements and phases are generated. These possible refinements/phases can be analyzed by the statistical model, which can output a probabilistic distribution over each of the possible refinements/phases. A refinement/phase found to be most probable can be selected and the low resolution HLA data can be replaced with the selected high resolution HLA data.

Other aspects will be appreciated upon reading and understanding the attached figures and description.

BRIEF DESCRIPTION OF THE DRAWINGS

FIG. 3 is an example data set of unphased high resolution HLA data.

FIG. 4 is an example phased high resolution data set for a particular patient.

DETAILED DESCRIPTION

Figure 1:
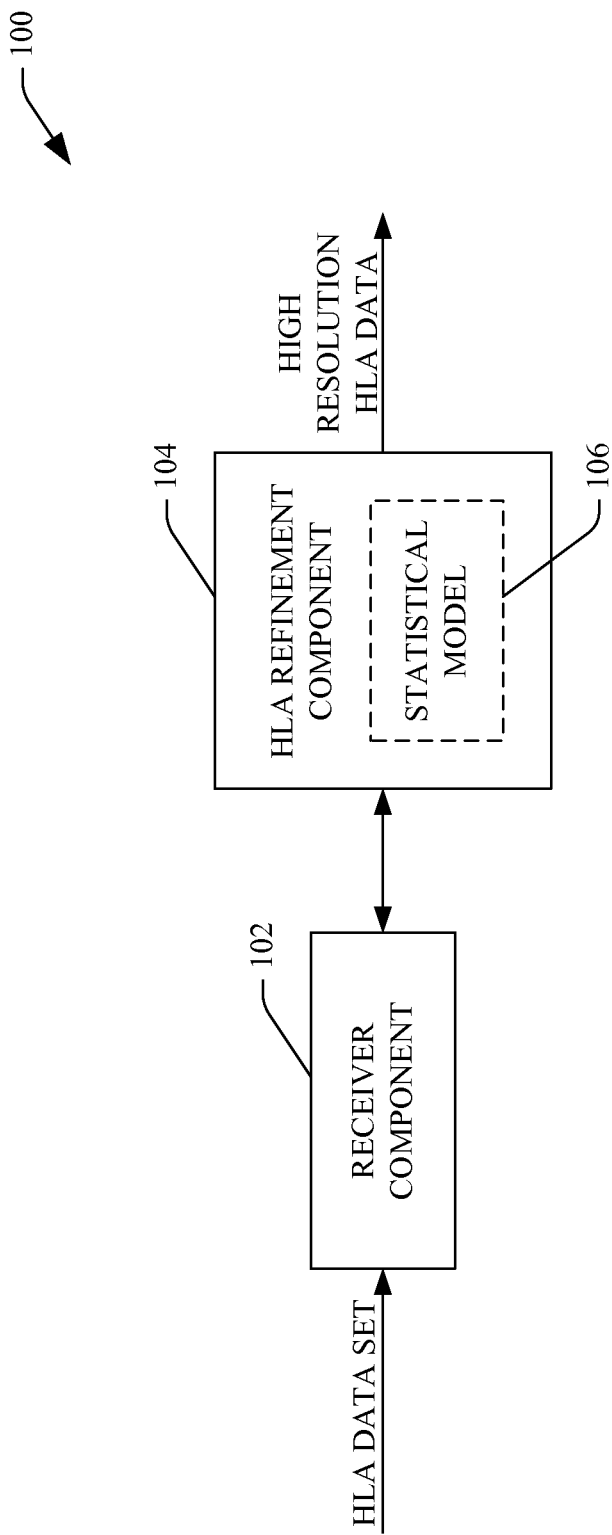
FIG. 1 is a functional block diagram of an example system that facilitates transforming low resolution HLA data to high resolution HLA data.

Various technologies pertaining to refining HLA data (automatically transforming low resolution HLA data to high resolution HLA data) will now be described with reference to the drawings, where like reference numerals represent like elements throughout. In addition, several functional block diagrams of example systems are illustrated and described herein for purposes of explanation; however, it is to be understood that functionality that is described as being carried out by certain system components may be performed by multiple components. Similarly, for instance, a component may be configured to perform functionality that is described as being carried out by multiple components.

With reference to FIG. 1, an example system 100 that facilitates refining an HLA data set is illustrated. The system 100 includes a receiver component 102 that receives an HLA data set, wherein the HLA data set comprises low resolution HLA data. For purposes of explanation HLA nomenclature will be described. HLA nomenclature is closely tied with levels of possible HLA ambiguity. Specifically, each HLA allele is assigned a letter or letters which designate a particular locus. For instance, for a Class I HLA allele, letters A, B or C can be assigned to an allele. For Class II alleles, letters DRA, DRB1, DRB2-9, DQA1, DQB1, DPA1 or DPB1 can be assigned. This letter or letters is followed by a sequence of numbers. The first two digits of the sequence of numbers describe the allele type. The third and fourth digits can be used to designate the allele subtypes, wherein alleles are assigned numbers from 01 through 99 roughly according to their order of discovery. Thus, four digits can uniquely define an allele: by definition, any two alleles which differ in their four digit number differ by at least one amino acid.

It is to be understood that more than four digits can be used to designate an allele in accordance with conventional nomenclature. Fifth and sixth digits can be used to distinguish alleles which differ only by synonymous substitutions (e.g., do not change the amino acid sequence of the protein). Seventh and eighth digits can distinguish alleles which differ in sequence in noncoating regions of a gene (e.g., introns or the 5' or 3' untranslated regions). Thus, pursuant to an example, A*0301 can designate an allele at the A locus. As used herein, low resolution HLA data can refer to HLA data resolved to two numerical digits to represent allele types in accordance with the conventional nomenclature, and high resolution HLA data can refer to HLA data resolved to four or more numerical digits to represent allele subtypes in accordance with the conventional nomenclature. As noted, high resolution HLA data may also refer to HLA data resolved to six numerical digits or eight numerical digits. Moreover, using the systems/methods described herein, HLA data resolved to zero digits may be resolved to two digits, four digits, six digits, etc. Similarly, HLA data resolved to two digits may be resolved to four digits, six digits, etc. using the systems/methods described herein.

Additionally, the HLA data set received by the receiver component 102 may include phased HLA data and/or unphased HLA data. With respect to HLA data of Class I, an individual can receive HLA alleles from a chromosome from each of the individual's parents. In some instances, however, children can receive mosaics of parental DNA rather than exact copies of parental DNA. Accordingly, for HLA data of Class I, it is often known that an individual includes two particular A alleles resolved to two numerical digits, two particular B alleles resolved to two numerical digits, and two particular C alleles resolve to two numerical digits, but it is unknown how such alleles align with one another along the pair of chromosomes inherited from the parents. Therefore, the HLA data set may include information indicative of a person having the following alleles: A1, A2, B1, B2, C1, C2 for the A, B and C loci, respectively. It may not be known, however, that A1, B2 and C1 correspond to a first chromosome of the individual and A2, B1 and C2 correspond to a second chromosome of the individual. As used herein, unphased HLA data refers to HLA data for particular alleles that are not known to be on a particular chromosome and phased HLA data refers to HLA data resolved into certain haplotypes.

The system 100 further includes an HLA refinement component 104 that is in communication with the receiver component 102. The HLA refinement component 104 can comprise a statistical model 106, wherein the statistical model 106 can automatically refine the HLA data set received by the receiver component 102 to transform the low resolution HLA data in the HLA data set to high resolution HLA data. For instance the statistical model 106 can be trained through use of an expectation-maximization algorithm, a Monte Carlo algorithm or other suitable algorithm that can be used in connection with machine learning. Furthermore the statistical model 106 may be or include a neural network, a Bayesian belief model, a support vector machine, a nearest neighbor algorithm or other suitable machine learning algorithms/components. Training of the statistical model 106 will be described in greater detail below.

Pursuant to a particular example, the statistical model 106 may be trained using high resolution HLA data that is phased or high resolution HLA data that is unphased, or some combination of high resolution phased and unphased data. Additionally, the statistical model 106 can be trained using HLA data that corresponds to a particular ethnicity and/or geographic region. For instance, particular ethnicities are known to have certain types/subtypes of HLA alleles and thus a model trained using HLA data pertaining to particular ethnicity may be better suited to refine HLA data pertaining to such ethnicity. Moreover, the statistical model 106 can output phased high resolution HLA data and/or unphased high resolution HLA data. As will be described in greater detail herein, the statistical model 106 may assign probabilistic distributions to a plurality of possible allele subtype combinations, and the subtype combination with the highest probability distribution can be selected as the proper HLA haplotype.

Figure 2:
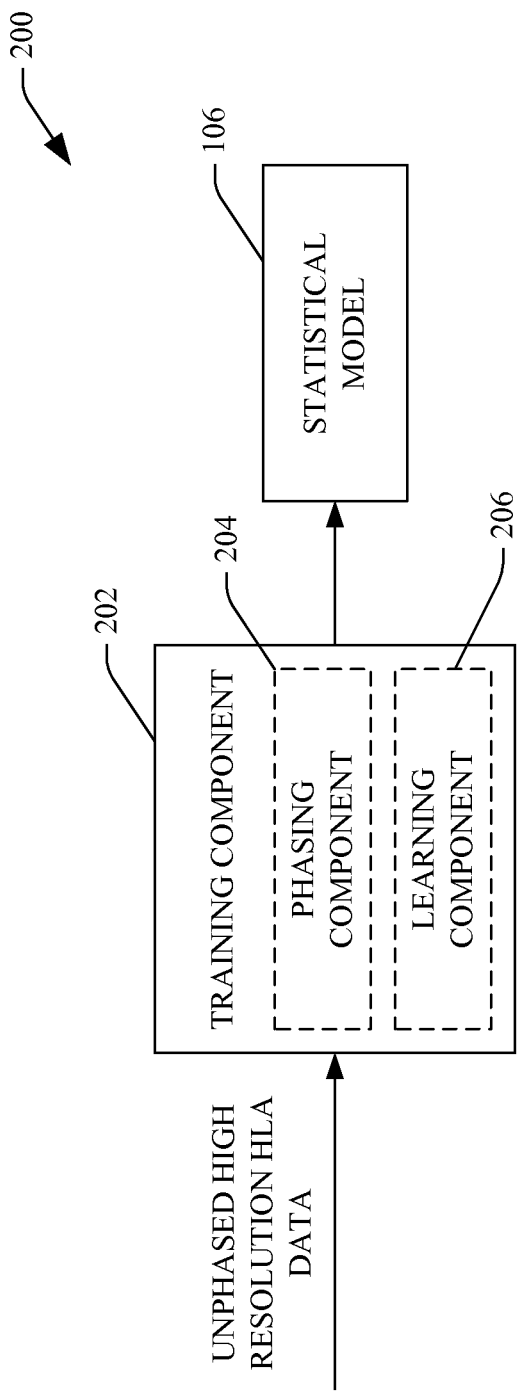
FIG. 2 is a functional block diagram of an example system that facilitates training a model that can be used in connection with automatically transforming low resolution HLA data to high resolution HLA data.

Referring now to FIG. 2, an example system 200 that facilitates training the statistical model 106 is illustrated. The system 200 includes a training component 202 that is configured to receive unphased high resolution HLA data. Additionally or alternatively, the training component 202 may receive phased high resolution HLA data. The training component 202 includes a phasing component 204 that phases the unphased high resolution HLA data into haplotypes. That is, with respect to a single patient in the unphased high resolution data, the phasing component 204 can phase HLA data pertaining to such patient into two haplotypes, one for each chromosome. The training component 202 can additionally include a learning component 206 that learns statistical patterns present in the high resolution HLA data received by the training component 202. In other words, the training component 202 can jointly phase and build the statistical model 106.

Prior to explaining operation of the training component 202 in detail, a standard expectation-maximization based model that can be used in connection with phasing unphased high resolution data (haplotype inference) is explained. In an example, haplotype inference can be performed over three loci, $L_1$, $L_2$ and $L_3$, with $L^i (i \in \{1,2,3\})$ alleles at each locus. In an exemplary expectation-maximization based approach, the probability of a haplotype can be parameterized by a multinomial table which can provide the probability for every possible haplotype $p(l_1, l_2, l_3) = p_{l_1 l_2 l_3}$. In such an example there would be $L = \Pi_i L^i$ possible haplotypes requiring L parameters $p_{l_1 l_2 l_3}$. Generally, expectation-maximization algorithms are general algorithms for solving ML/MAP parameter estimates in the presence of missing data/hidden variables (which, here, are the phases). In the context of inferring haplotypes, expectation maximization can reduce to iterating between two steps. Step 1: given the parameter estimates (for $\{p_{l_1 l_2 l_3}\}$), find a distribution of phases for each observed genotype. This can be referred to as the E-step, where the expectation over haplotypes/hidden states is computed. Step 2: given the distribution over haplotypes/hidden states for each observed genotype, compute the maximum likelihood parameter estimate (the multinomial parameters). This is the M-step, where the parameters are maximized with respect to the expected complete log likelihood, where the expectation is taken with respect to the posterior over hidden states and the complete log likelihood is the likelihood in which the missing information (the phase) has been probabilistically completed proportionally to the posterior distribution over phases.

In both cases, it is assumed that the probability of an individual's genotype data having a particular phasing is the probability of each of the two haplotypes defined by the phasing. Thus, such an approach assumes Hardy-Weinberg equilibrium.

There are two possible problems with using such a modeling approach in connection with the training component 202. The first is that the number of parameters L scales poorly with the number of loci and with the number of alleles at each locus. This creates two practical problems which may come into play: computational limitations on the number of loci/alleles which can be handled by the algorithm and poor stability with respect to the parameter estimation, because the number of parameters tends to be very large relative to the number of data typically available. The training component 202 can be configured to alleviate such problems.

An example model that can be used by the phasing component 204 that uses fewer parameters than the aforementioned full multinomial table is described herein. Such a model can be a model for $p(l_1, l_2, l_3)$. It is to be understood, however, that the model can be extended for any suitable number of loci. Using the chain rule for probability, $p(l_1, l_2, l_3)$ can be expressed as:

$$p(l_1, l_2, l_3) = p(l_1)p(l_2|l_1)p(l_3|l_1,l_2).$$

It can be noted that such expression does not introduce any conditional independencies. If a conditional probability table were to be used for each of these three local distributions, then such a model would capture the same information as $p(l_1, l_1, l_3) = p_{l_1 l_2 l_3}$ and would not reduce the number of parameters. Instead of using conditional probability tables, however, a multi-logit regression function (also known as a softmax regression function) can be employed by the training component 202. Such a multi-logit regression function can be an extension of logistic regression to more than two target classes. Using a softmax or multi-logit function to parameterize $p(l_3 = \alpha_k | l_1, l_2)$, the probability that the allele at the third locus is the kth allele, conditioned on the alleles at the other two loci $l_1, l_2$, the following can be obtained:

$$p(l_3 = k \mid l_1, l_2) = \frac{\exp(w_1^k l_1 + w_2^k l_2 + w_0^k)}{\sum_{j=1}^{L^3} \exp(w_1^j l_1 + w_2^j l_2 + w_0^j)},$$

where $w^j=(w_0^j, w_1^j, w_2^j)$ are parameter vectors of the multi-logit regression, one for each possible allele j at the third locus. Thus, the multi-logit regression function used by the training component 202 can take a linear combination of the input features $w_1^j l_1 + w_2^j l_2$, plus a constant term $w_0^j$, to model each class, which produces a real valued number for each class. Then this real value can be exponentiated and normalized relative to all of the other classes to yield the probability of interest. Similarly, the multi-logit regression function for $p(l_2|l_1)$ can be written as:

$$p(l_2 = k \mid l_1) = \frac{\exp(v^k l_1 + v_0^k)}{\sum_{j=1}^{L^2} \exp(v_1^j l_1 + v_0^j)},$$

and the multi-logit regression function for $p(l_1)$ can be written as:

$$p(l_1 = k) = \frac{\exp(q_0^k)}{\sum_{j=1}^{L^1} \exp(q_0^j)}$$

with respective parameters $v^j=(v_0^j, v_1^j)$ and $q_0^j$. It can be understood that a generalized multi-logit regression function that can be used for each locus being modeled can be used by the training component 202 (e.g., for any suitable number of loci). For example, a generalized function for an nth locus can be as follows:

$$p(l_n = k \mid l_1, l_2, \ldots l_{n-1}) = \frac{\exp(w_{n-1}^k l_{n-1} + \ldots + w_1^k l_1 + w_2^k l_2 + w_0^k)}{\sum_{j=1}^{L^N} \exp(w_{n-1}^k l_{n-1} + \ldots + w_1^k l_1 + w_2^k l_2 + w_0^k)},$$

where $p(l_n = k | l_1, l_2, \ldots, l_{n-1})$ is the probability that an allele at the nth locus is the kth possible allele and $w^j=(w_0^j, w_1^j, w_2^j, \ldots, w_{n-1}^j)$ is a parameter vector for each possible allele j at the nth locus.

Because the alleles at each locus are discreet in nature, the training component 202 may use a binarized version of the inputs. That is, one hot encoding can be used, wherein each discreet input $l_1 = k$ can be represented by a binary vector of length $L^i$ that contains all zeros except at the kth position (which can include a one). Correspondingly, the parameter vectors can be augmented in length to match such dimensionality. Therefore, in this binary representation, the length of each $w^k$ would be $L^1 + L^2 + 1$, and a total number of scalar parameters required to represent $p(l_1, l_2, l_3)$ would be $M = L^3(L_1 + L^2 + 1) + L^2(L^1 + 1) + L^1(1)$. It can be ascertained that M grows much more slowly here as compared to L for the multinomial tables. In particular, L grows exponentially in the number of loci and alleles, whereas M grows only linearly. Use of full tables versus a multi-logit regression function relates to the well known bias variance tradeoff which states that the more flexible a model, the more variance one will have in estimating its parameters. To reduce variance, the flexibility of the model can be decreased (e.g., by using a multi-logit regression rather than multinomial parameterizations), thereby increasing the bias of the statistical model 106 (because the family of possible models is more restricted). Whether a suitable bias variance tradeoff has been selected can be assessed empirically.

Additionally, the multi-logit regression model can be extended to more than three loci (e.g., to N loci) and can be extended more efficiently than a multinomial based model. It can further be noted that the additive nature of the multi-logit regression function can lead to a property that similar haplotypes have similar joint probabilities. Coalescent priors used in some Bayesian approaches also have this property whereas full tables do not. Thus, in one example implementation, the phasing component 204 can access or include a multi-logit regression model that can be used in connection with inferring phase of unphased high resolution HLA data.

As noted above, the learning component 206 can use an expectation-maximization algorithm to train the statistical model 106. In other words, the learning component 206 can use an expectation-maximization algorithm to choose settings of the multi-logit regression parameters $w^j$, $v^j$, and $q^j$ given observed genotype data. The way that the learning component 206 uses the expectation-maximization algorithm is similar to the way in which such an algorithm would operate in connection with multinomial based models. Thus, the learning component 206 can use an expectation-maximization algorithm to iterate between an E step, where the posterior over possible faces is computed, followed by an M step, where the parameters of the model are computed based on the posterior computations from the E step. The difference is that the posterior uses the multi-logit regression model to compute the posterior and the M step estimates multi-logit regression parameters rather than multinomial parameters.

Formally $g^d$ can be the observed genotype/HLA data for the $d^{th}$ person in the high resolution HLA data received by the training component 202. For instance, if the unphased high resolution HLA data includes data for three loci HLA-A, HLA-B and HLA-C, then the unphased high resolution HLA data includes unphased data for each chromosome for each locus:

$$g^d = (g_{A1}^d, g_{A2}^d, g_{B1}^d, g_{B2}^d, g_{C1}^d, g_{C2}^d).$$

Accordingly, there are $2^{number\ of\ loci-1}$ possible unique phase states $h_i^d$ that can be taken on by such data (assuming no ordering of the chromosomes).

$$h_1^d = \{(g_{A1}^d, g_{B1}^d, g_{C1}^d), (g_{A2}^d, g_{B2}^d, g_{C2}^d)\}$$

$$h_2^d = \{(g_{A1}^d, g_{B2}^d, g_{C1}^d), (g_{A2}^d, g_{B1}^d, g_{C2}^d)\}$$

$$h_3^d = \{(g_{A1}^d, g_{B1}^d, g_{C2}^d), (g_{A2}^d, g_{B2}^d, g_{C1}^d)\}$$

$$h_4^d = \{(g_{A1}^d, g_{B2}^d, g_{C2}^d), (g_{A2}^d, g_{B1}^d, g_{C1}^d)\}$$

For the E step, the phasing component 204 can compute p(hd $i^d|g^d$) for each data point for each possible phase. The phasing component 204 can undertake such computation by determining the likelihood of the data in each possible phase state and then renormalizing these within each person so that $\Sigma_i p(h_i^d|g^d)=1$. Pursuant to an example, the phasing component 204 can assume that each phasing is a priori equi-probable. The phasing component 204 can additionally compute the likelihood of one datum in a particular phase state $l_i^d$ by determining the product of the likelihood under the aforementioned haplotype model for each of the two chromosomes. For example, the phasing component 204 can compute the likelihood for the $d^{th}$ genotype to be in phase state two using the following:

$$l_2^d = p(g_{A1}^d, g_{B2}^d, g_{C1}^d) p(g_{A2}^d, g_{B1}^d, g_{C2}^d).$$

The phasing component 204 can additionally renormalize these likelihoods to output the posterior over phase states for a single individual $$p(h_i^d | g^d) = \frac{l_i^d}{\sum_j l_j^d}.$$

The learning component 206 can be used in connection with performing the M step. Specifically, the learning component 206 can use the E step posteriors output by the phasing component 204 to compute parameter estimates. In an example, the learning component 206 can use MAP parameter estimates. Additionally, for the prior distribution of each parameter, the learning component 206 can employ a zero centered Gaussian distribution. The learning component 206 can maximize the following quantity with respect to the parameters $w^j$, $v^j$, and $q^j$:

$$L_{L_2}^C = L^C - \lambda_1 \sum_{j=1}^{L^1} \|w^j\|^2 - \lambda_2 \sum_{j=1}^{L^2} \|v^j\|^2 - \lambda_3 \|q^j\|^2$$

where $\|x\|$ denotes the L2 norm of vector x. This quantity is the regularized expected complete log likelihood. The regularization parameters $\lambda = (\lambda_1, \lambda_2, \lambda_3)$, which are (inversely) related to the variance of the Gaussian prior, can be set empirically using a holdout set. Because this MAP estimation issue is embedded inside of an M step, the regularization parameters are theoretically not independent (except for $\lambda_1$ because it does not depend on the phasing of the data) and hence can be adjusted jointly.

It is to be understood that other parameters priors can be used by the training component 202 in connection with training the statistical model 106. For instance, a Laplacian prior can be used. In another example, L1 regularization can be used. Iterating between the E step and the M step using the phasing component 204 and the learning component 206 from some chosen parameter initialization (or some posterior initialization), the log posterior of the data L can be locally maximized (keeping the $\lambda_j$ fixed) as follows:

$$L(\lambda) = \left[ \sum_{person\ d} \log \sum_{phase\ i} l_i^d \right] - \lambda_1 \sum_{j=1}^{L^1} \|w^j\|^2 - \lambda_2 \sum_{j=1}^{L^2} \|v^j\|^2 - \lambda_2 \sum_{j=1}^{L_3} \|q^j\|^2$$

Additionally or alternatively, the parameters of the multinomial table can be smoothed/regularized using a Dirichlet prior. Such smoothing may add pseudo counts to the observed count of the data when computing the ML estimate during the M step.

Of course, other methodologies/mechanisms are contemplated in connection with training the statistical model 106. For instance, a support vector machine, a naïve Bayesian network, an artificial neural network, a k-nearest neighbor approach or other suitable algorithm/mechanism can be used in connection with training the statistical model 106, and expectation-maximization is just but one exemplary mechanism/algorithm for training such model 106.

Furthermore, while the statistical model 106 and training thereof has been described with respect to HLA data, it is to be understood that the statistical model 106 can be trained and used in connection with other genetic data where phasing is desired, such as Single Nucleotide Polymorphisms.

With reference now to FIG. 3, an example data set that includes unphased high resolution data for a plurality of different patients/individuals is illustrated. The HLA data in the exemplary data set 300 pertains to three loci HLA-A, HLA-B and HLA-C for two different chromosomes per patient. As noted above, training and using the statistical model 106 is not limited to cases where such three loci are of interest, as the statistical model 106 can be trained and used in connection with additional loci as well as Class II HLA data. As can be ascertained, for each patient high resolution HLA data is obtained for two chromosomes for three different Class I loci: HLA-A, HLA-B and HLA-C. It can also be ascertained that such HLA data is unphased, as the data includes no indication of which HLA data corresponds to a certain chromosome. This exemplary data may be used in connection with training the statistical model 106.

With reference to FIG. 4, an exemplary data set 400 is illustrated. This data set includes HLA data for a single patient for three different loci HLA-A, HLA-B and HLA-C. It can be discerned the data in the data set 400 is phased as A*0201, B*2705 and C*0703 correspond to a first chromosome and A*6801, B*0701 and C*0701 correspond to a second chromosome of the patient. As noted above, phasing can be inferred with respect to data used to train the statistical model 106. Additionally, phased high resolution data can be output by the statistical model 106 upon receipt of unphased data, wherein at least part of the unphased data is low resolution HLA data.

Figure 5:
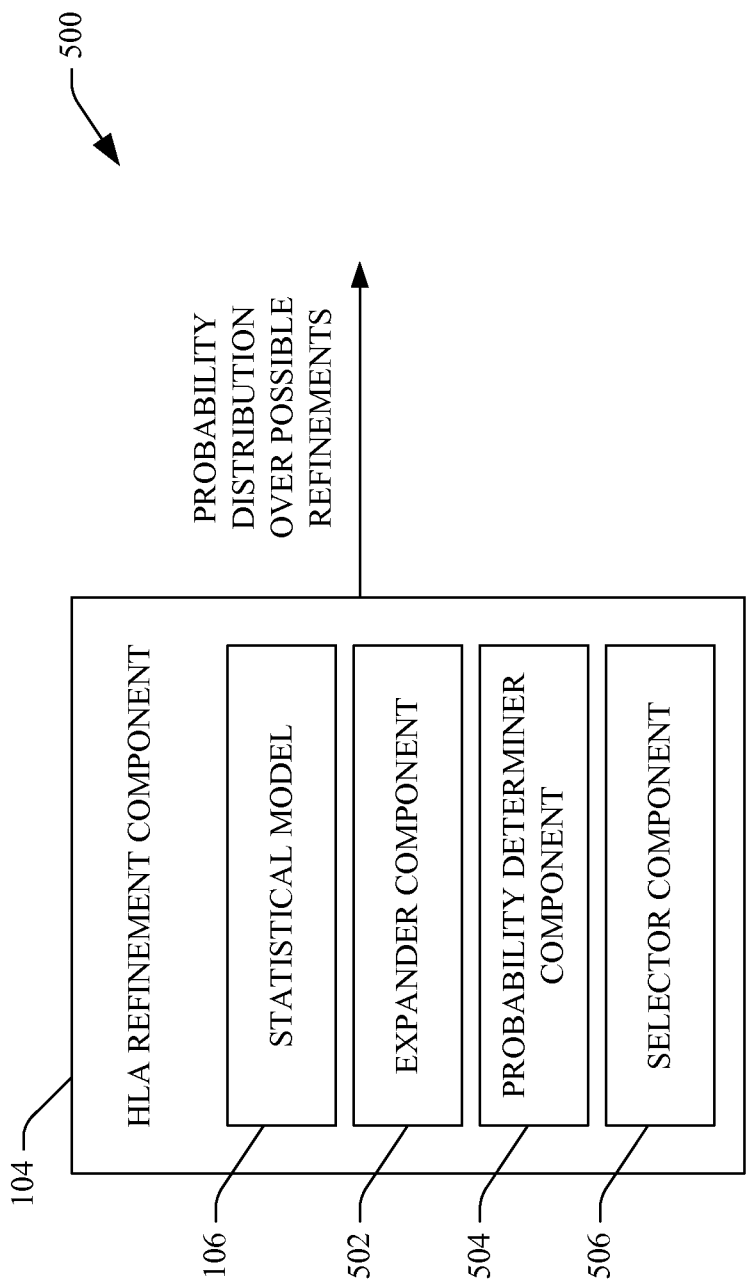
FIG. 5 is a functional block diagram of an example component that can output probability distribution over possible HLA refinements.

With reference now to FIG. 5, an expanded depiction 500 of the HLA refinement component 104 is illustrated. As described above, the statistical model 106 is trained using an expectation-maximization algorithm on a data set that includes high resolution HLA data, wherein such HLA data may correspond to a population similar to that of a data set of interest (e.g., similar ethnic background, similar geography, etc.). Using the statistical model 106, the HLA refinement component 104 can probabilistically refine an HLA data set that includes low resolution data. To undertake such probabilistic refinement, the HLA refinement component 104 refines each person's HLA type independently of another person's HLA type in the data set of interest. To accomplish the foregoing, the HLA refinement component 104 includes an expander component 502 that receives unphased data, wherein at least a portion of the unphased data is of low resolution. The expander component 502 expands the unphased data into a plurality of possible phases. In an example, the expander component 502 can exhaustively output a list of all possible unique phases (including the low-resolution HLA data) that are consistent with each person's observed genotype data. Thereafter, the expander component 502 can output a list of all possible unique four-digit phases (including only high resolution data) that are consistent with each person's observed genotype. Thus, the expander component 502 can output all possible (mixed resolution) phases, and thereafter expand each of such phases to all possible four-digit phases. In an example, if one person's observed genotype in a data set of interest is the following:

$$g^d=(A*30,A*3002,B*57,B*0801,Cw*0401,Cw*1502)),$$

then the expander component 502 can output the following:

$$h_1^d=\{(A*30,B*57,Cw*0401),(A*3002,B*0801,Cw*1502)\}$$

$$h_2^d=\{(A*30,B*0801,Cw*0401),(A*3002,B*57,Cw*1502)\}$$

$$h_3^d=\{(A*30,B*57,Cw*1502),(A*3002,B*0801,Cw*0401)\}$$

$$h_4^d=\{(A*30,B*0801,Cw*1502),(A*3002,B*57,Cw*0401)\}.$$

The expander component 502 may then further expand such data. For instance, the expander component 502 can further expand $h_1^d$ as follows:

$$h_1^d(1)=\{(A*3001,B*5701,Cw*0401),(A*3002,B*0801,Cw*1502)\}$$

$$h_1^d(2)=\{(A*3002,B*5701,Cw*0401),(A*3002,B*0801,Cw*1502)\}$$

$$\ldots$$

$$h_1^d(j)=\{(A*3030,B*5701,Cw*0401),(A*3002,B*0801,Cw*1502)\}$$

$$h_1^d(j+1)=\{(A*3030,B*5701,Cw*0401),(A*3002,B*0801,Cw*1502)\}$$

$$\ldots$$

$$h_1^d(j+k)=\{(A*3030,B*5701,Cw*0401),(A*3002,B*0801,Cw*1502)\}$$

$$\ldots$$

$$h_1^d(j^1)=\{(A*3030,B*5701,Cw*0401),(A*3002,B*0801,Cw*1502)\}$$

Similarly, the expander component 502 can further expand hid to obtain additional $j^2, j^3$, and $j^4$ possible four-digit phasings. The total number of possible four-digit phasings consistent with this person's observed genotype is thus $j=j^1+j^2+j^3+j^4$. Additionally or alternatively, if the data set of interest includes genotype ambiguity (in the form of possible pairs of alleles) then the expander component 502 can expand the data in all possible ways consistent with those pairs.

The HLA refinement component 104 can additionally include a probability determiner component 504 that can ascertain a probability distribution over possible refinements output by the expander component 502 to provide a relative probability for each possible refinement. For instance, the probability determiner component 504 can sum posterior probabilities of members of the list output by the expander component 502 that are consistent with each observed genotype. For example, $\{(A*3030, B*5713, Cw*0401), (A*3002, B*0801, Cw*1502)\}$ and $\{(A*3002, B*5713, Cw*0401), (A*3030, B*0801, Cw*1502)\}$ would give rise to the same observed genotype $\{(A*3030, A*3002, B*5713, B*0801, Cw*0401, Cw*1502)\}$ and accordingly, the probability determiner component 504 can sum together posterior probabilities corresponding to $\{(A*3030, B*5713, Cw*0401), (A*3002, B*0801, Cw*1502)\}$ and $\{(A*3002, B*5713, Cw*0401), (A*3030, B*0801, Cw*1502)\}$ (along with any other entries in the list which map the same observed genotype) to obtain the posterior probability of that genotype.

The HLA refinement component 104 can additionally include a selector component 506 that can select in an automated manner the genotype that has the highest probability for inclusion in an output data set. As noted above, the probability determiner component 504 can output a probability distribution over all possible four-digit genotypes. The selector component 506 can select the observed genotype that is assigned the highest probability by the probability determiner component 504 and can include such genotype in the output HLA data set. While the probability determiner component 504 is shown as being separate from the statistical model 106, it is to be understood that the statistical model 106 can include the probability determiner component 504 and functionality corresponding thereto. Thus, the HLA refinement component 104 can output a refined HLA data set that includes, for each person in the received HLA data set, a most probable genotype.

Figure 6:
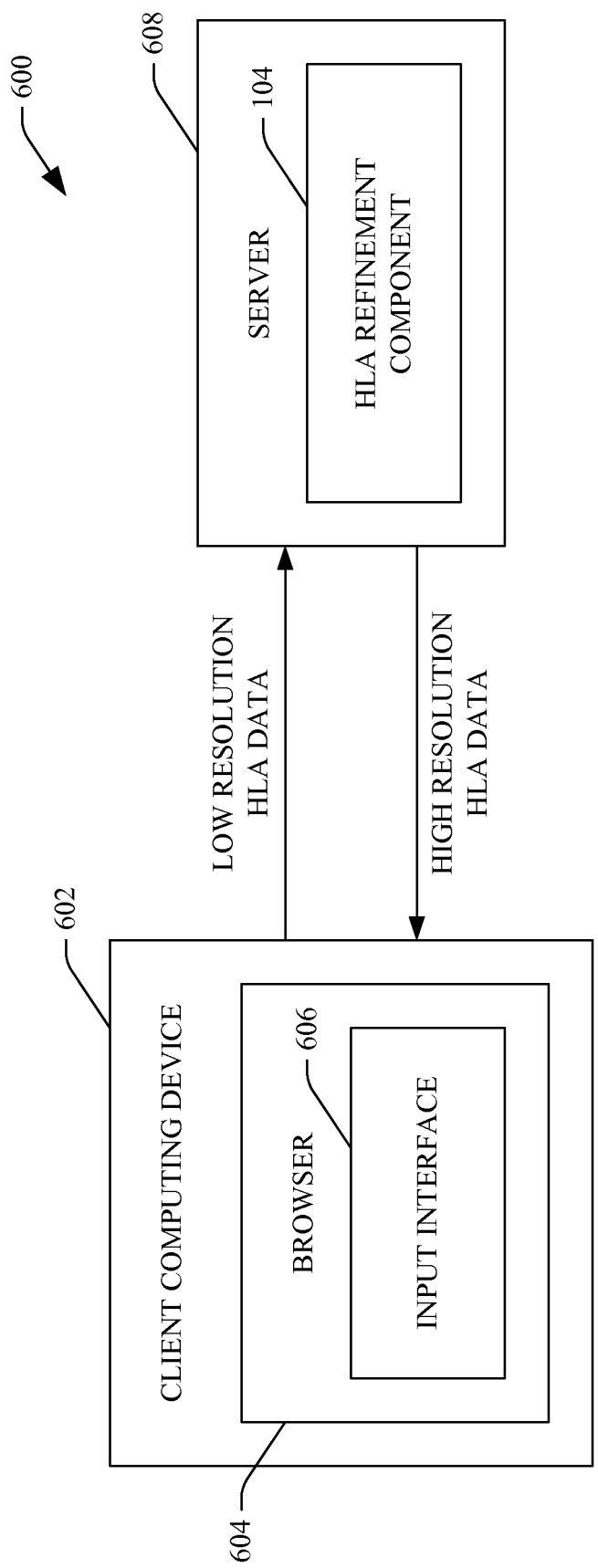
FIG. 6 is a functional block diagram of an example system that facilitates receiving low resolution HLA data by way of a web browser.

Referring now to FIG. 6, an example system 600 that facilitates refining low resolution HLA data is illustrated. The system 600 includes a client computing device 602, which can be a desktop computer, a laptop computer, a personal digital assistant or other suitable computing device. In an example, the client computing device 602 may have a browser 604 installed thereon, wherein the browser 604 may be used in connection with accessing web pages/web services. For instance, the browser 604 can be used to display a web page to the user that includes an input interface 606. The input interface 606 can be configured to receive, for instance, a data set that comprises low resolution HLA data. The input interface 606 can be configured to accept text files, files formatted in accordance with spreadsheet applications, etc.

The client computer device 602 can be in communication with a server 608 by way of any suitable communication network. The server 608 is shown to include the HLA refinement component 104. The HLA refinement component 104 can receive the low resolution HLA data from the client computing device 602 by way of a network connection. The HLA refinement component 104 may then act as described above, in connection with refining the low resolution HLA data to transform such low resolution HLA data into high resolution HLA data. The high resolution HLA data can then be transferred to the client computing device 602 and displayed to a user of the client computing device 602 as a web page in the browser 604. Thus, an individual with access to HLA data that includes low resolution HLA data can refine such data through use of a service provided by way of the Internet, for example.

While not shown, it is to be understood that the HLA refinement component 104 may be configured for execution in a client side application. Thus, a user may install a client application on the client computing device 602 and refine low resolution HLA data locally.

With reference now to FIGS. 7-10, example methodologies are illustrated and described. While the methodologies are described as being a series of acts that are performed in a sequence, it is to be understood that the methodologies are not limited by the order of the sequence. For instance, some acts may occur in a different order than what is described herein. In addition, an act may occur concurrently with another act. Furthermore, in some instances, not all acts may be required to implement a methodology described herein.

Moreover, the acts described herein may be computer-executable instructions that can be implemented by one or more processors and/or stored on a computer-readable medium or media. The computer-executable instructions may include a routine, a sub-routine, programs, a thread of execution, and/or the like. Thus, the computer-executable instructions, when executed by a processor, can cause the processor to perform a variety of acts. Still further, results of acts of the methodologies may be stored in a computer-readable medium, displayed on a display device, and/or the like.

Figure 7:
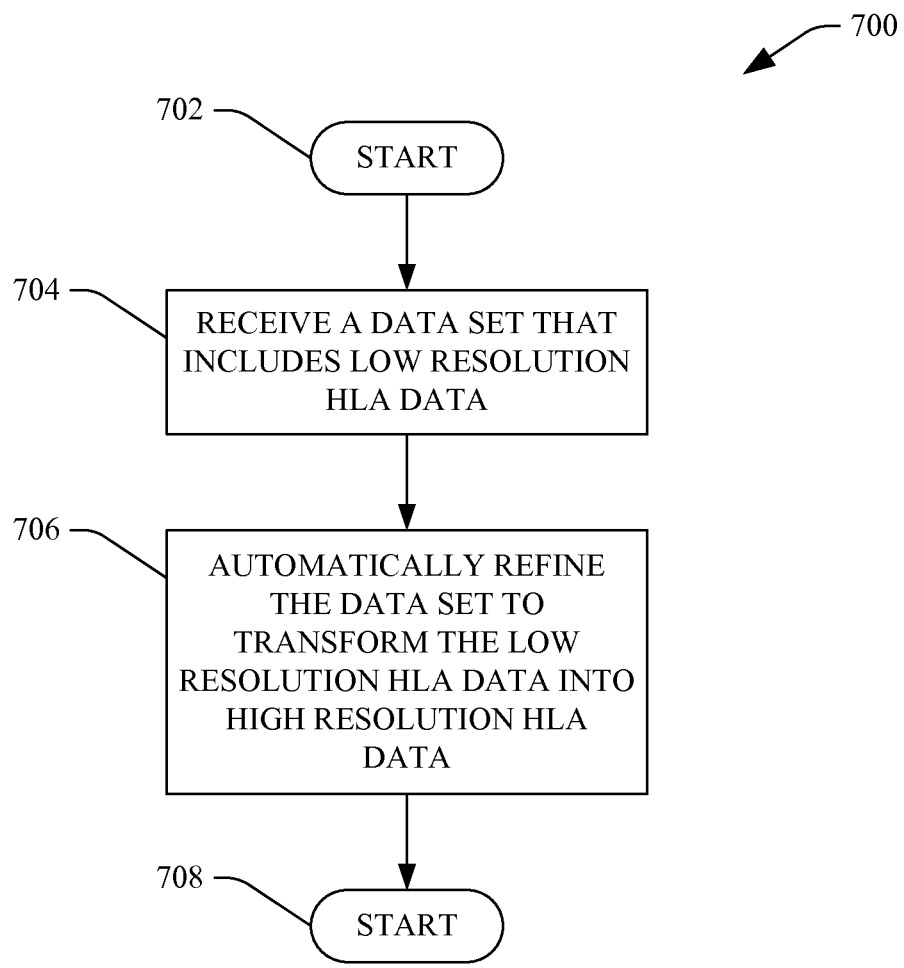
FIG. 7 is a flow diagram that illustrates an example methodology for automatically refining low resolution HLA data.

Referring now to FIG. 7, an example methodology 700 that facilitates automatically transforming low resolution HLA data to high resolution HLA data is illustrated. The methodology 700 begins at 702, and at 704 a data set is received, wherein the data set includes low resolution HLA data. Additionally, the data set may include high resolution HLA data.

At 706, the low resolution HLA data is automatically refined to transform the low resolution HLA data into high resolution HLA data. For instance, such automatic refinement can be undertaken through use of a statistical model. As noted above, the statistical model may be trained using an expectation-maximization algorithm or through use of another suitable training algorithm. The methodology 700 completes at 708.

Figure 8:
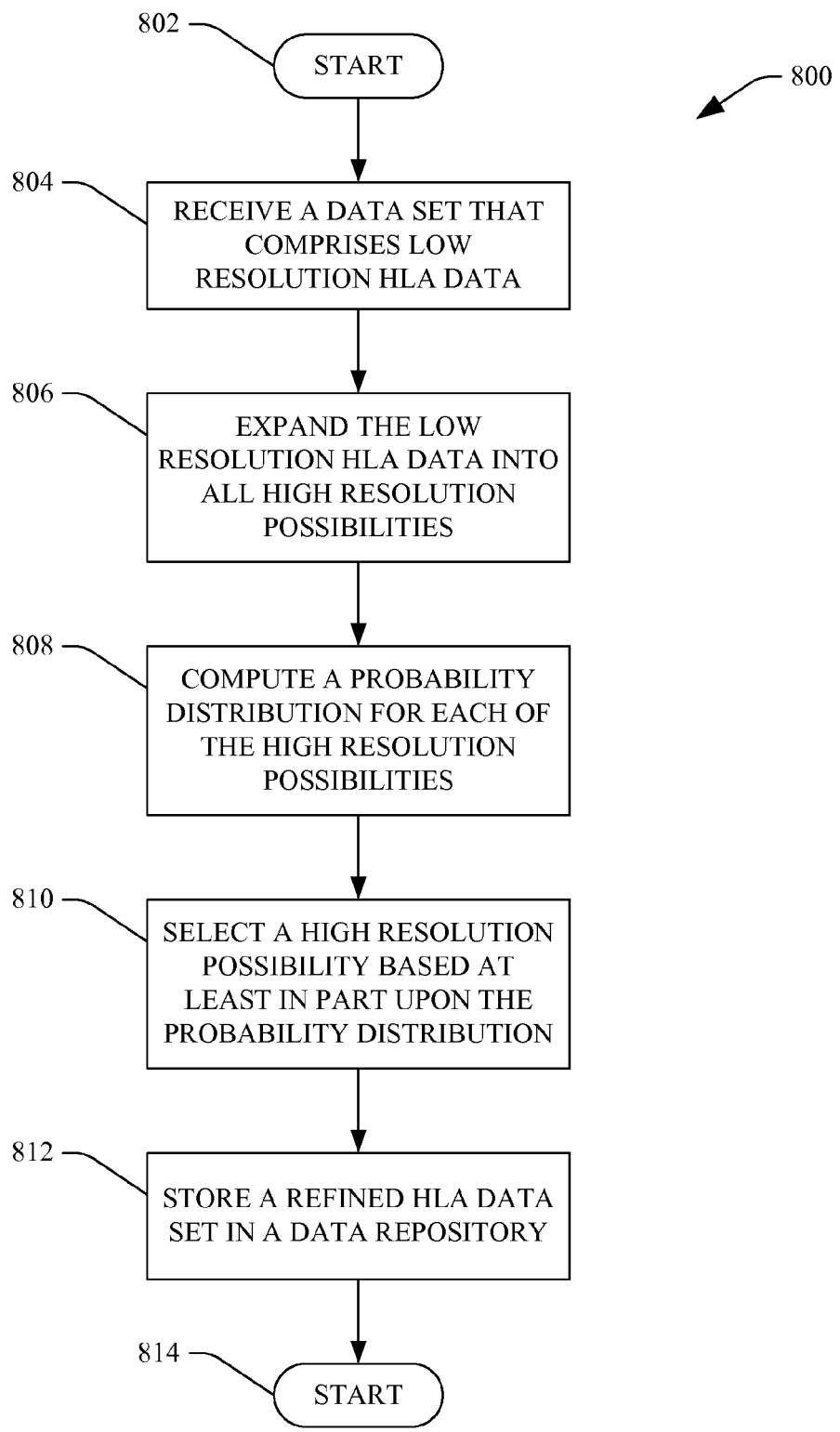
FIG. 8 is a flow diagram that illustrates an example methodology for automatically transforming low resolution HLA data to high resolution HLA data.

With reference now to FIG. 8, an example methodology 800 for automatically refining low resolution data in an HLA data set is illustrated. The methodology 800 starts at 802, and at 804 a data set that comprises low resolution HLA data is received. As noted above, low resolution HLA data can refer to HLA data that is resolved to two numerical digits to represent allele types.

At 806, the data set is expanded such that low resolution HLA data is expanded to a plurality of possible HLA refinements. For instance, the low resolution HLA data can be expanded to all high resolution possibilities for the low resolution HLA data.

At 808, a probability distribution for each of the high resolution possibilities of the low resolution HLA data is computed through use of a statistical model. In other words, machine learning can be used in connection with outputting a probability distribution for all high resolution possibilities of the low resolution HLA data.

At 810, a high resolution possibility (determined through expanding low resolution data) is selected based at least in part upon the computed probability distribution to generate refined HLA data. The computation of the probability distribution and the selection can be undertaken individually for data corresponding to different patients.

At 812 the refined HLA data set is stored in a data repository. Such refined HLA data set may be used in connection with researching HLA data over particular population with respect to certain diseases, etc. The methodology completes at 814.

Figure 9:
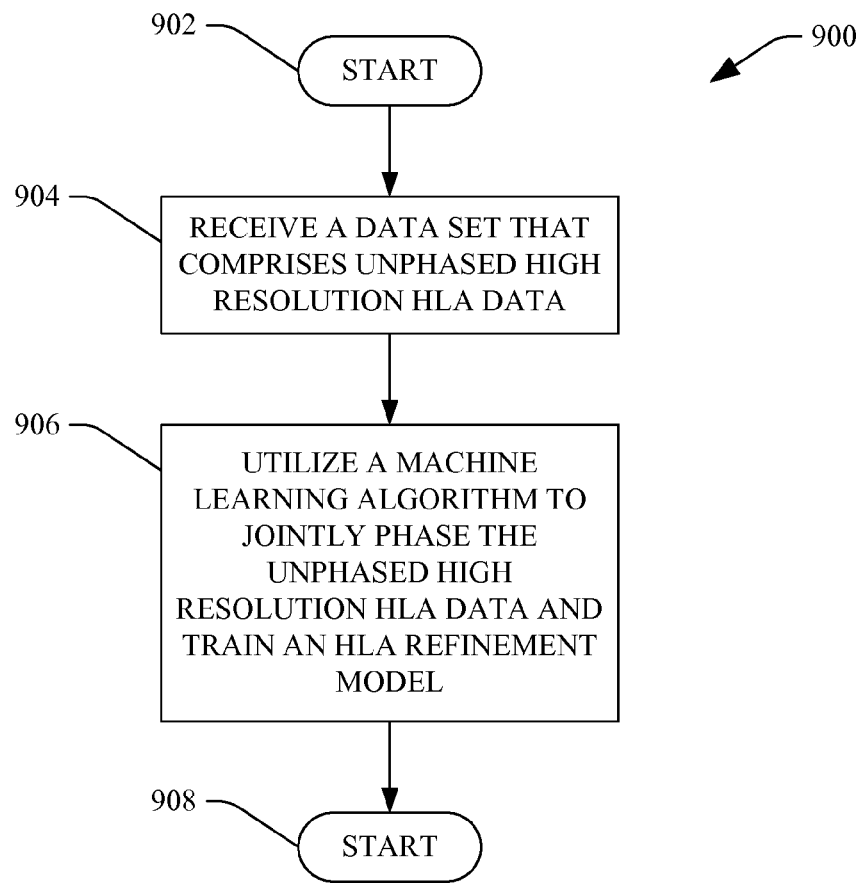
FIG. 9 is a flow diagram that illustrates an example methodology for using machine learning techniques to train a model for refining low resolution HLA data.

Turning now to FIG. 9, an example methodology 900 that facilities training a model used in connection with refining low resolution HLA data is illustrated. The methodology 900 starts at 902, and at 904 a data set is received, wherein the data set includes unphased high resolution HLA data. In an example, the data set may consist entirely of unphased high resolution HLA data. In another example, the received data set may include both phased and unphased high resolution HLA data. In still yet another example, the entire data set may consist solely of high resolution HLA data.

At 906, a machine learning algorithm is used to jointly phase the unphased high resolution HLA data and train an HLA refinement model. For instance, the machine learning algorithm may be an expectation-maximization algorithm, may be or include a Bayesian network, a support vector machine, etc. The trained HLA refinement model may then be used to refine low resolution HLA data to high resolution HLA data. The methodology 900 completes at 908.

Figure 10:
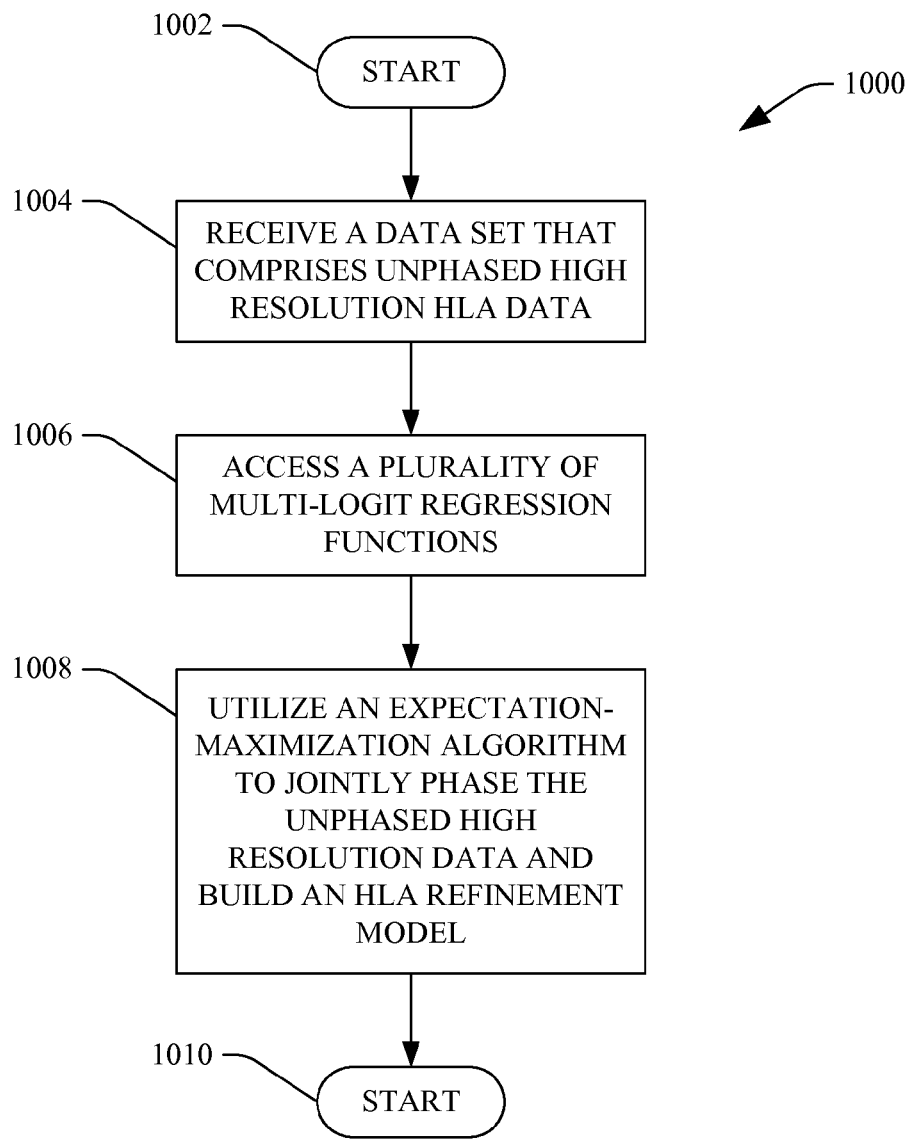
FIG. 10 is a flow diagram that illustrates an example methodology for using an expectation-maximization algorithm to jointly phase unphased high resolution data and build an HLA refinement model.

Referring now to FIG. 10, an example methodology 1000 for building/training an HLA refinement model is illustrated. The methodology 1000 starts at 1002, and at 1004 a data set that comprises unphased high resolution HLA data is received. For instance the data set may solely consist of unphased high resolution HLA data.

At 1006, a plurality of multi-logit regression functions are accessed. For instance, these multi-logit regression functions may be retained in a memory of a computing device.

At 1008, an expectation-maximization algorithm is utilized to jointly phase the unphased high resolution data and build an HLA refinement model. The methodology 1000 completes at 1010.

Figure 11:
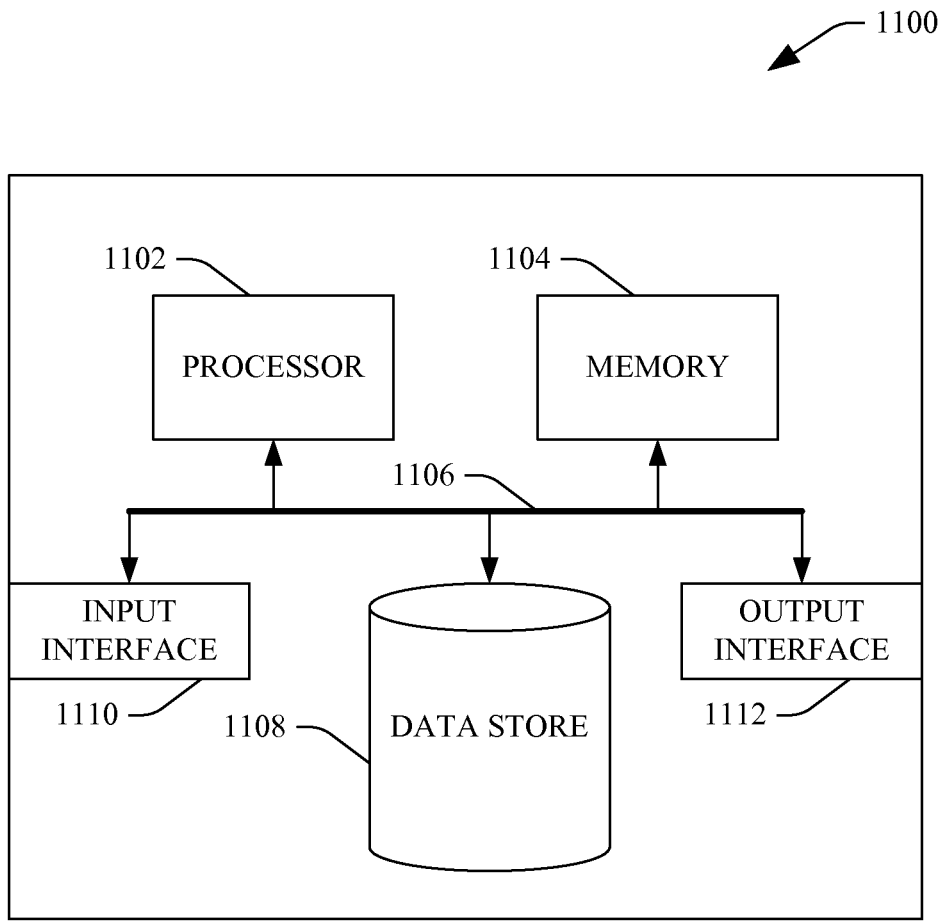
FIG. 11 is an example computing system.

Now referring to FIG. 11, a high-level illustration of an example computing device 1100 that can be used in accordance with the systems and methodologies disclosed herein is illustrated. For instance, the computing device 1100 may be used in a system that supports refining low resolution HLA data. In another example, at least a portion of the computing device 1100 may be used in a system that supports training an HLA refinement model. The computing device 1100 includes at least one processor 1102 that executes instructions that are stored in a memory 1104. The instructions may be, for instance, instructions for implementing functionality described as being carried out by one or more components discussed above or instructions for implementing one or more of the methods described above. The processor 1102 may access the memory 1104 by way of a system bus 1106. In addition to storing executable instructions, the memory 1104 may also store low resolution HLA data, high resolution HLA data, phased HLA data, unphased HLA data, etc.

The computing device 1100 additionally includes a data store 1108 that is accessible by the processor 1102 by way of the system bus 1106. The data store 1108 may include executable instructions, HLA data, multi-logit algorithms, etc. The computing device 1100 also includes an input interface 1110 that allows external devices to communicate with the computing device 1100. For instance, the input interface 1110 may be used to receive instructions from an external computer device. The computing device 1100 also includes an output interface 1112 that interfaces the computing device 1100 with one or more external devices. For example, the computing device 1100 may display text, images, etc. by way of the output interface 1112.

While the description above pertained to refining HLA data at the level of alleles, it is to be understood that the systems/methods described above can be used for HLA refinement at the nucleotide level.

Additionally, while illustrated as a single system, it is to be understood that the computing device 1100 may be a distributed system. Thus, for instance, several devices may be in communication by way of a network connection and may collectively perform tasks described as being performed by the computing device 1100.

As used herein, the terms "component" and "system" are intended to encompass hardware, software, or a combination of hardware and software. Thus, for example, a system or component may be a process, a process executing on a processor, or a processor. Additionally, a component or system may be localized on a single device or distributed across several devices. Thus, the components described herein may be computer-executable in nature.

It is noted that several examples have been provided for purposes of explanation. These examples are not to be construed as limiting the hereto-appended claims. Additionally, it may be recognized that the examples provided herein may be permutated while still falling under the scope of the claims.

What is claimed is:

1. A system comprising:
   a processor; and
   a memory that comprises a plurality of components that are executed by the processor, the plurality of components comprising:
   a receiver component that receives a Human Leukocyte Antigen (HLA) data set, wherein the HLA data set comprises low resolution HLA data of at least one patient, wherein the low resolution HLA data identifies allele types of HLA genes of the at least one patient but fails to identify allele subtypes of the HLA genes of the at least one patient; and
   an HLA refinement component that comprises a statistical model that automatically refines the HLA data set to transform the low resolution HLA data to high resolution HLA data that identifies the allele subtypes of the HLA genes of the at least one patient.

2. The system of claim 1, wherein the statistical model is trained using high resolution HLA data.

3. The system of claim 1, wherein the statistical model is trained by way of an expectation-maximization algorithm.

4. The system of claim 1, wherein the statistical model is trained by way of a Monte Carlo algorithm.

5. The system of claim 1, wherein the statistical model is trained with HLA data of individuals of multiple ethnic backgrounds.

6. The system of claim 1, wherein the statistical model is trained with unphased high resolution HLA data, wherein unphased HLA data is HLA data that fails to include identifiers for haplotypes of HLA genes represented in the HLA data.

7. The system of claim 6, wherein the refinement component comprises a multi-logit regression function that infers phases of the unphased HLA data.

8. The system of claim 7, wherein the multi-logit regression function infers phases of the unphased HLA data for each locus being modeled, and wherein the function for an nth locus is $$p(l_n = k \mid l_1, l_2, \ldots l_{n-1}) = \frac{\exp(w_{n-1}^k l_{n-1} + \ldots + w_1^k l_1 + w_2^k l_2 + w_0^k)}{\sum_{j=1}^{L^N} \exp(w_{n-1}^k l_{n-1} + \ldots + w_1^k l_1 + w_2^k l_2 + w_0^k)},$$

where $p(l_n = k \mid l_1, l_2, \ldots l_{n-1})$ is the probability that an allele at the nth locus is the kth possible allele and $w^j = (w_0^j, w_1^j, w_2^j, \ldots w_{n-1}^j)$ is a parameter vector for each possible allele j at the nth locus.

9. The system of claim 1, wherein the refinement component comprises an expander component that receives unphased HLA data, wherein unphased HLA data is HLA data that fails to include identifiers for haplotypes of HLA genes represented in the HLA data, wherein at least a portion of the unphased HLA data is of low resolution, and wherein the expander component expands the unphased HLA data into a plurality of possible phases, the plurality of possible phases identifying possible haplotypes of the HLA genes represented in the HLA data, wherein the plurality of possible phases include low resolution HLA data.

10. The system of claim 9, wherein the expander component additionally expands each of the plurality of possible phases into pluralities of possible phases of high resolution HLA data.

11. The system of claim 10, wherein the refinement component comprises a probability determiner component that computes a probability distribution over the possible phases of high resolution HLA data to indicate which of the possible phases of high resolution HLA data is a most likely phase.

12. The system of claim 11, wherein the probability determiner component sums probabilities of refinements for each observed genotype to provide a relative probability for each possible refinement.

13. A method comprising the following computer-executable acts:
   receiving a data set, wherein the data set comprises low resolution Human Leukocyte Antigen (HLA) data, wherein low resolution HLA data refers to data representative of HLA genes of at least one individual that identifies allele types of the HLA genes but fails to identify allele subtypes of the HLA genes of the individual; and
   executing, with a processor, computer-executable code that causes the low resolution HLA data to be transformed to high resolution HLA data, wherein high resolution HLA data refers to data representative of HLA genes of the at least one individual that identifies allele types and allele subtypes of the HLA genes.

14. The method of claim 13, wherein the data set is received by way of a web browser.

15. A computer-readable storage medium comprising instructions that, when executed by a processor, cause the processor to perform acts comprising:
   receiving a data set that comprises low resolution Human Leukocyte Antigen (HLA) data, wherein low resolution HLA data is HLA data that is resolved to two numerical digits to represent allele types;
   expanding the data set such that the low resolution HLA data is expanded to a plurality of possible HLA refinements;
   computing a probability distribution for each possible HLA refinement to indicate probabilistically which HLA refinement is a most likely refinement;
   selecting at least one HLA refinement based upon the computed probability distributions to generate a refined HLA data set; and
   causing the refined HLA data set to be stored in a data repository.

16. The method of claim 13, wherein the computer-executable code comprises a computer-executable statistical model that probabilistically computes the high resolution HLA data.

17. The method of claim 16, wherein the computer-executable statistical model is trained with an expectation-maximization algorithm.

18. The method of claim 13, further comprising inferring haplotypes of the HLA genes of the at least one individual.

19. The method of claim 13 configured for execution on a server accessible by a web browser.

20. The computer-readable storage medium of claim 15, wherein the at least one HLA refinement comprises identifying an HLA gene of at least one individual by allele type and allele subtype.

* * * * *

UNITED STATES PATENT AND TRADEMARK OFFICE
CERTIFICATE OF CORRECTION

PATENT NO. : 8,473,218 B2
APPLICATION NO. : 12/431786
DATED : June 25, 2013
INVENTOR(S) : Jennifer Listgarten et al.

It is certified that error appears in the above-identified patent and that said Letters Patent is hereby corrected as shown below:

In the Specification

In column 6, line 2, delete "$W_1^{j}l_1 + w_2^{j}l_2,$" and insert -- $w_1^{j}l_1 + w_2^{j}l_2,$ --, therefor.

In column 9, line 60, delete "))" and insert -- ) --, therefor.

In column 10, line 29, after ")}" insert -- . --.

In the Claims

In column 14, line 63, In Claim 11, delete "likely phase" and insert -- probable phase from amongst the possible phases of high resolution HLA data --, therefor.

In column 16, line 6, In Claim 15, delete "likely refinement" and insert -- probable HLA refinement --, therefor.

In column 16, line 7, in Claim 15, delete "at least one" and insert -- the most probable --, therefor.

In column 16, lines 7-8, in Claim 15, after "refinement" delete "based upon the computed probability distributions".

Signed and Sealed this
Twenty-fourth Day of February, 2015

Michelle K. Lee
*Deputy Director of the United States Patent and Trademark Office*